United States Patent [19]

Untch

[11] 3,975,427

[45] Aug. 17, 1976

[54] METHOD FOR PREPARATION OF (dl)-13-SUBSTITUTED SULFINYL-PROSTAGLANDIN-LIKE COMPOUNDS

[75] Inventor: Karl G. Untch, Los Altos, Calif.

[73] Assignee: Syntex (U.S.A.) Inc., Palo Alto, Calif.

[22] Filed: June 5, 1974

[21] Appl. No.: 476,363

[52] U.S. Cl. ............................... 260/470; 260/400; 260/402; 260/468 D; 260/520 R; 424/305; 424/308

[51] Int. Cl.² ........................................ C07C 147/14

[58] Field of Search ............... 260/520, 470, 468 D, 260/400, 402

[56] References Cited
UNITED STATES PATENTS 2,862,946   12/1958   Kharasch ........................... 260/456

OTHER PUBLICATIONS

Baldwin et al., *Chem. Commun.*, pp. 538–539, (1968).
Bickart et al., *J. Amer. Chem. Soc.*, 90, pp. 4869–4876, (1968).
Miller et al., *J. Amer. Chem. Soc.*, 96, pp. 6774–6775, (10/16/74).
Zefirov et al., I, *J. Org. Chem*, USSR, 7, pp. 962–965, (1971).
Zefirov et al., II, *Chem. Abst.*, 71:112345p, (1969).
Zefirov et al., III, *Chem. Abst.*, 74:125046d, (1971).
Allinger et al., *Organic Chemistry*, pp. 574–575, (1971).

*Primary Examiner*—Lorraine A. Weinberger
*Assistant Examiner*—Michael Shippen
*Attorney, Agent, or Firm*—William B. Walker; Gerard A. Blaufarb

[57] ABSTRACT

(dl)-13-Substituted sulfinyl-prostaglandin-like [(dl)-2α-substituted-3β-(1α-substituted sulfinyl-trans-2-alkenyl)-1-oxygenated cyclopentane and (dl)-2α-substituted-3β-(1α-substituted sulfinyl-trans-2-alkenyl-4α-hydroxy-1-oxygenated cyclopentane]compounds exhibiting prostaglandin-like biological properties are prepared from known prostaglandins and prostaglandin-like compounds.

16 Claims, No Drawings

METHOD FOR PREPARATION OF (D1)-13-SUBSTITUTED SULFINYL-PROSTAGLANDIN-LIKE COMPOUNDS

SUMMARY OF THE INVENTION

The (dl)-13-substituted sulfinyl-prostaglandin-like [(dl)-2α-substituted -3β-(1α-substituted sulfinyl-trans-2-alkenyl)-1-oxygenated cyclopentane and (dl)-2α-substituted-3β-(1α-substituted sulfinyl-trans-2-alkenyl)-4α-hydroxy-1-oxygenated cyclopentane] compounds of the formulas:

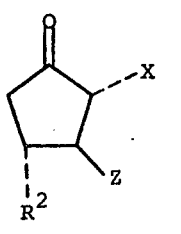 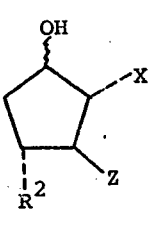

(A) (B)

wherein:
R² is hydrogen or hydroxyl;
X is

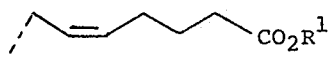

or - - - (CH₂)$_m$CO₂R¹, in which R¹ is alkyl containing from one through three carbon atoms, and m is a whole integer from two through eight;
Z is

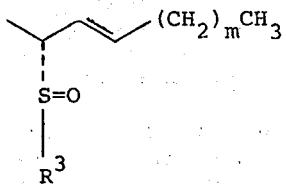

in which R³ is alkyl containing from one through six carbon atoms, cycloalkyl containing from five through seven carbon atoms, chloromethyl, trichloromethyl, trifluoromethyl, chlorodifluoromethyl, dichlorofluoromethyl, β-chloroethyl, α-chloroethyl, α-chloro-β-trichloroethyl, phenyl, p-tolyl, p-chlorophenyl, p-fluorophenyl, 2,4-dichlorophenyl, or 2,5-dichlorophenyl; and m is defined as above; and
the wavy line (ξ) represents the α or β configuration or mixtures thereof, are disclosed in copending application Ser. No. 476,362, filed June 5, 1974. The present invention relates to a novel process for the preparation of the compounds of Formulas (A) and (B) from known prostaglandin and prostaglandin-like compounds.

BACKGROUND OF THE INVENTION

1. The Invention

This invention relates to a novel process for the preparation of (dl)-13-substituted sulfinyl-prostaglandin-like [(dl)-2α-substituted-3β-(1α-substituted sulfinyl-trans-2-alkenyl)-1-oxygenated cyclopentane and (dl)-2α-substituted-3β-(1α-substituted sulfinyl-trans-2-alkenyl)-4α-hydroxy-1-oxygenated cyclopentane] compounds.

More particularly, it relates to a novel process for the preparation of the prostaglandin-like compounds of Formulas (A) and (B) above (whose nomenclature is discussed more fully below) from known prostaglandin and prostaglandin-like compounds.

2. The Prior Art

Prostaglandins have classically been described as chemically related 20-carbon chain hydroxy fatty acids having the basic skeleton of prostanoic acid:

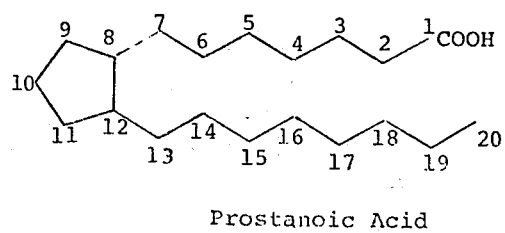

Prostanoic Acid

The prostaglandins having an hydroxyl group at the C-11 position and a keto group at the C-9 position are known as the PGE series, those having an hydroxyl group in place of the keto group are known as the PGF series and are further designated by α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, PGE₁ refers to a prostanoic acid having a trans olefin bond at the 13-position. For a review on prostaglandins and the definition of primary prostaglandins, see, for example, S. Bergstrom, Recent Progress in *Hormone Research* 22, pp. 153–175 (1966) and *Science* 157, page 382 (1967) by the same author.

Prostaglandins are widely distributed in mammalian tissues and have been isolated from natural sources in very small amounts. In addition a number of the natural occurring prostaglandins have been prepared by chemical synthesis; note, for example, *J. Am. Chem. Soc.* 91, 5675 (1969), *J. Am. Chem. Soc.* 92, 2586 (1970) and *J. Am. Chem. Soc.* 93, 1489–1493 (1971) and references cited therein, W.P. Schneider et al., *J. Am. Chem. Soc.* 90, 5895 (1968) U. Axen et al., *Chem. Commun.*, 303 (1969), and W.P. Schneider, *Chem. Commun.*, 304 (1969).

Because of the remarkable range of biological and pharmacological properties exhibited by this family of compounds, a great deal of interest has focused upon such compounds and accordingly we have discovered a novel process for the preparation of (dl)-13-sulfinyl-prostaglandin-like [(dl)-2α-substituted-3β-(1α-substituted sulfinyl-trans-2-alkenyl)-1-oxygenated cyclopentane and (dl)-2α-substituted-3β-(1α-substituted sulfinyl-trans-2-alkenyl)-4α-hydroxy-1-oxygenated cyclopentane] compounds.

FURTHER DESCRIPTION OF THE INVENTION AND PREFERRED EMBODIMENTS

As discussed above prostaglandins have, for the most part, classically been named using as the base for such nomenclature the 20-carbon chain hydroxy fatty acids having the basic skeleton of prostanoic acid. For the naturally occurring prostaglandins this nomenclature has sufficed.

However, in view of the lengthening and shortening of the side chains (and the increased complexity of the side chains) attached at the C-2 and C-3 carbon atoms of the cyclopentane nucleus, as well as other substituents attached to the cyclopentane nucleus, it is readily apparent that a more systematic nomenclature must be used.

Therefore, in the description which follows, the compounds will be named as substituted cyclopentanes in which the cyclopentane nucleus will be numbered as follows:

Thus (dl)-PGE$_1$ having the structure

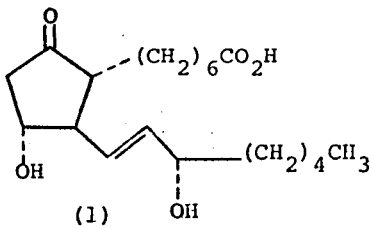

would be systematically named (dl)-2α-(6-carboxyhexyl)-3β-(3α-hydroxy-trans-1-octenyl)-4α-hydroxy-1-oxocyclopentane.

According to already established convention in the art, the chain attached to the C-3 carbon atom of the cyclopentane ring of naturally occurring prostaglandins having a trans double bond nearest to said C-3 carbon atom is depicted by structural configuration formula thusly

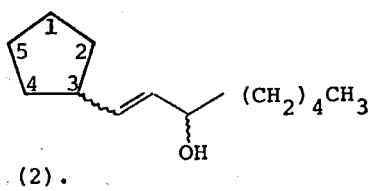

It is to be understood and will be apparent to those skilled in the art that the compounds of Formulas (A) and (B) above and (I) and (II) below exist as (dl) pairs. Thus, the (dl) pairs are a mixture of the d and l isomers. For example, the compounds of Formula (A) are actually a mixture of

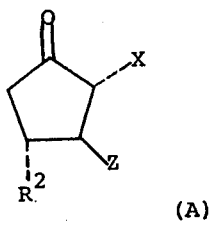

and its mirror images,

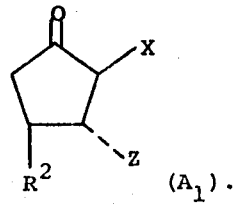

Again, to avoid undue prolixity, only one isomer, namely that analgous to that depicted by Formula (A), rather than Formula (A$_1$), will be shown, it being understood that in the specification and claims the mirror images are also encompassed thereby.

It is to be further understood that encompassed within this invention are racemic mixtures and diastereomeric mixtures.

The novel process for the production of the compounds of Formulas (A) and (B) is illustratively represented by the following reaction sequences:

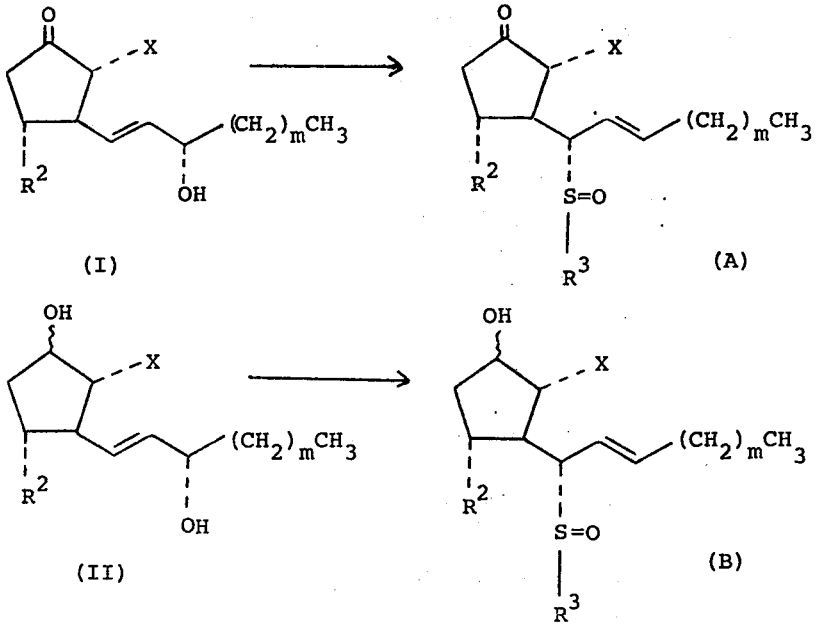

wherein X (including the definitions of $R^1$ and $m$ therein), $R^2$, $R^3$ and the wavy lines ($\xi$) are defined as above.

The terms "alkyl containing from one through six carbon atoms" or "alkyl containing from one through three carbon atoms" includes both straight and branched chain alkyl groups; and the broken line ($\vdots$) represents the $\alpha$-configuration.

In carrying out the process of our invention, the compounds of Formula (I) [and (II)] are reacted with a substituted sulfenyl chloride of the formula $ClSR^3$, wherein $R^3$ is defined as above, in the presence of an amine base e.g., triethylamine, N-methylpyrrolidine, pyridine, preferably, triethylamine, in an organic solvent, e.g., diethyl ether, tetrahydrofuran, dimethoxyethylene glycol, preferably diethyl ether, at a temperature of from 0°C to 35°C, preferably at room temperature (about 20°C), to obtain the compounds of Formula (A) [and (B)], respectively. Suitable substituted sulfenyl chlorides of the formula $ClSR^3$ are:

methylsulfenyl chloride,
ethylsulfenyl chloride,
propylsulfenyl chloride,
isopropylsulfenyl chloride,
n-butylsulfenyl chloride,
isobutylsulfenyl chloride,
n-pentylsulfenyl chloride,
isopentylsulfenyl chloride,
n-hexlsulfenyl chloride, and the like,
cyclopentylsulfenyl chloride,
cyclohexylsulfenyl chloride,
cycloheptylsulfenyl chloride,
chloromethylsulfenyl chloride,
trichloromethylsulfenyl chloride,
trifluoromethylsulfenyl chloride,
chlorodifluoromethylsulfenyl chloride,
dichlorofluoromethylsulfenyl chloride,
$\beta$-chloroethylsulfenyl chloride,
$\alpha$-chloroethylsulfenyl chloride,
$\alpha$-chloro-$\beta$-trichloroethylsulfenyl chloride,
benzenesulfenyl chloride,
p-toluenesulfenyl chloride,
p-chlorobenzenesulfenyl chloride,
2,4-dichlorobenzenesulfenyl chloride, and
2,5-dichlorobenzenesulfenyl chloride.

The compounds of Formulas (A) and (B) can, if desired, be converted to their corresponding free acids (and the non-toxic, pharmaceutically acceptable salts of the free acids) according to procedures disclosed in U.S. application Ser. No. 476,362, filed June 5, 1974.

The compounds of Formulas (A) and (B) exhibit prostaglandin-like biological activities and thus are useful in the treatment of mammals where the use of prostaglandins is indicated. The compounds (and the free acids corresponding thereto and the pharmaceutically acceptable salts of the free acids) are bronchodilators and thus are useful in treating mammals for bronchial spasm or wherever strong bronchodilators are indicated. The compounds are also useful in controlling or palliating hypertension in mammals and further exhibit central nervous system depressant activity, in mammals, and are useful as sedatives. In addition, the compounds are useful for inducing labor, in pregnancy, and for inducing means to correct or reduce menstrual abnormalities. The compounds also possess anti-fertility properties. In addition, they exhibit anti-inflammatory activities and thus are useful as anti-inflammatory agents.

The compounds of Formulas (A) and (B) (and the free acids corresponding thereto and the non-toxic, pharmaceutically acceptable salts of the free acids) can be administered in a wide variety of dosage forms, either alone or in combination with other pharmaceutically compatible medicaments, in the form of pharmaceutical compositions suited for oral or parenteral administration or inhalation in the case of bronchodilators. The compounds are typically administered as pharmaceutical compositions consisting essentially of the compounds and/or salts, of the invention, and a pharmaceutical carrier. The pharmaceutical carrier can be either a solid material, liquid, or aerosol, in which the compound and/or salt is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspension, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the compounds can, for example, be administered as an aerosol comprising the compounds or salts in an inert propellant together with a cosolvent (e.g., ethanol) together with optional preservatives and buffering agents. Additional general information concerning the inhalation administration of aerosols can be had by reference to U.S. Pat. Nos. 2,969,691 and 3,095,355.

The compounds of Formulas (A) and (B) (and the free acids corresponding thereto and the non-toxic pharmaceutically acceptable salts of the free acids) are typically administered in dosages of about from 0.01 to 10 mg. per kg. of body weight. The precise effective dosage will, of course, vary depending upon the mode of administration, condition being treated, and host.

It is to be understood that any of the compounds obtained can be separated and/or purified by any suitable separation and/or purification procedure, such as, for example, extraction, filtration, distillation, evaporation, crystallization, column chromatography, thin-layer chromatography, and the like. Specific illustrations of typical separation and/or purification procedures can be had by reference to the preparations and examples described herein below. However, other equivalent separation and/or purification procedures could, of course, also be used.

A further understanding of the invention can be had from the following non-limiting example.

EXAMPLE 1

To a solution of 70 mg. (0.20 mmole) of (dl)-2$\alpha$-(6-carboemethoxyhexyl)-3$\beta$-(3$\alpha$-hydroxy-trans-1-octenyl)-1-oxo-cyclopentane (I) dissolved in 20 ml. of dry diethyl ether containing 76 mg. (0.75 mmole) of triethylamine there is added 40 mg. (0.25 mmole) of freshly distilled p-toluenesulfenyl chloride. The reaction mixture is stirred at room temperature until the yellow color disappears (about 20 minutes) and monitored by thin-layer chromatography. After completion of the reaction, as measured by thin-layer chromatography, the precipitate formed is filtered, and the filtrate thus-obtained is concentrated and purified by preparative thin-layer chromatography (eluting with ethyl acetate: hexane::2:3) to yield (dl)-2α-(6-carbomethoxyhexyl)-3β-(1α-p-tolylsulfinyl-trans-2-octenyl)-1-oxocyclopentane (A), which is further purified by column chromatography (using ethyl acetate:hexane) or crystallization from ether:hexane.

Similarly, substituting an equivalent amount of other starting materials of Formulas (I) and (II) for (dl)-2α-(6-carbomethoxyhexyl)-3β-(3α-hydroxy-trans-1-octenyl)-1-oxocyclopentane, for example, (dl)-2α-(6-carbomethoxy-cis-2-hexenyl)-3β-(3α-hydroxy-trans-1-octenyl)-1-oxocyclopentane, (dl)-2α-(6-carbomethoxyhexyl)-3β-(3α-hydroxy-trans-1-octenyl)-4α-hydroxy-1-oxocyclopentane, (dl)-2α-(6-carbomethoxy-cis-2-hexenyl)-3β-(3α-hydroxy-trans-1-octenyl)-4α-hydroxy-1-oxocyclopentane, (dl)-2α-(6-carbomethoxyhexyl)-3β-(3α-hydroxy-trans-1-octenyl)-1α-hydroxycyclopentane, (dl)-2α-(6-carbomethoxyhexyl)-3β-(3α-hydroxy-trans-1-octenyl)-1β-hydroxycyclopentane, (dl)-2α-(6-carbomethoxy-cis-2-hexenyl)-3β-(3α-hydroxy-trans-1-octenyl)-1α-hydroxycyclopentane, (dl)-2α-(6-carbomethoxy-cis-2-hexenyl)-3β-(3α-hydroxy-trans-1-octenyl)-1β-hydroxycyclopentane.

(dl)-2α-(6-carbomethoxyhexyl)-3β-(3α-hydroxy-trans-1-octenyl)-4α-hydroxy-1α-hydroxycyclopentane, (dl)-2α-(6-carbomethoxyhexyl)-3β-(3α-hydroxy-trans-1-octenyl)-4α-hydroxy-1β-hydroxycyclopentane, (dl)-2α-(6-carbomethoxy-cis-2-hexenyl)-3β-(3α-hydroxy-trans-1-octenyl)-4α-hydroxy-1α-hydroxycyclopentane, and (dl)-2α-(6-carbomethoxy-cis-2-hexenyl)-3β-(3α-hydroxy-trans-1-octenyl)-4α-hydroxy-1β-hydroxycyclopentane, is productive of (dl)-2α-(6-carbomethoxy-cis-2-hexenyl)-3β-(1α-p-tolylsulfinyl-trans-2-octenyl)-1-oxocyclopentane, (dl)-2α-(6-carbomethoxyhexyl)-3β-(1α-p-tolylsulfinyl-trans-2-octenyl)-4α-hydroxy-1-oxocyclopentane, (dl)-2a-(6-carbomethoxy-cis-2-hexenyl)-3β(1α-p-tolylsulfinyl-trans-2-octenyl)-4α-hydroxy-1-oxocyclopentane, (dl)-2α-(6-carbomethoxyhexyl)-3β-(1α-p-tolylsulfinyl-trans-2-octenyl)-1α-hydroxycyclopentane, (dl)-2α-(6-carbomethoxyhexyl)-3β-(1α-p-tolylsulfinyl-trans-2-octenyl)-1β-hydroxycyclopentane, (dl)-2α-(6-carbomethoxy-cis-2-hexenyl)-3β-(1α-p-tolylsulfinyl-trans-2-octenyl)-1α-hydroxycyclopentane, (dl)-2α-(6-carbomethoxy-cis-2-hexenyl)-3β-(1α-p-tolylsulfinyl-trans-2-octenyl)-1β-hydroxycyclopentane, (dl)-2α-(6-carbomethoxyhexyl)-3β-(1α-p-tolylsulfinyl-trans-2-octenyl)-4α-hydroxy-1α-hydroxycyclopentane, (dl)-2α-(6-carbomethoxyhexyl)-3β-(1α-p-tolylsulfinyl-trans-2-octenyl)-4α-hydroxy-1β-hydroxycyclopentane, (dl)-2α-(6-carbomethoxy-cis-2-hexenyl)-3β(1α-p-tolylsulfinyl-trans-2-octenyl)-4α-hydroxy-1α-hydroxycyclopentane, and (dl)-2α-(6-carbomethoxy-cis-2-hexenyl)-3β-(1α-p-tolylsulfinyl-trans-2-octenyl)-4α-hydroxy-1β-hydroxycyclopentane, respectively.

Likewise, other substituted sulfenyl chlorides substituted for p-toluenesulfenyl chloride, and using the compounds of Formulas (I) and (II) is productive of the corresponding 3β-(1α-substituted sulfinyl-trans-2-alkenyl)compounds of Formulas (A) and (B).

Obviously many modifications of the invention described herein above and below in claims can be made without departing from the essence and scope thereof.

What is claimed is:

1. Process for the production of the (dl) compounds of the formulas:

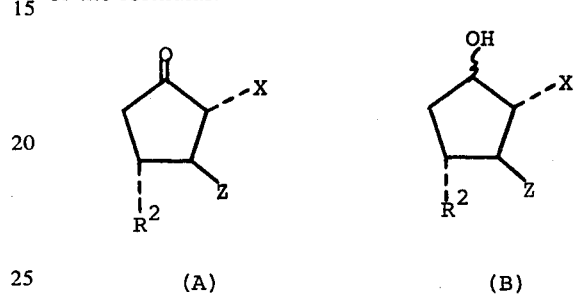

(A)              (B)

wherein X is

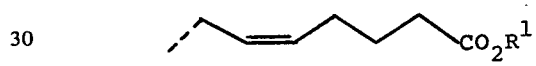

or - - - $(CH_2)_m CO_2 R^1$, in which $R^1$ is alkyl containing from one through three carbon atoms, and $m$ is a whole integer from two through eight;

$R^2$ is hydrogen or hydroxyl;

Z is

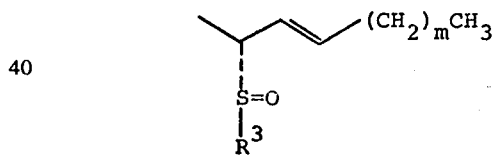

in which $R^3$ is alkyl containing from one through six carbon atoms, cycloalkyl containing from five through seven carbon atoms, chloromethyl, trichloromethyl, trifluoromethyl, chlorodifluoromethyl, dichlorofluoromethyl, β-chloroethyl, α-chloroethyl, α-chloro-β-trichloroethyl, phenyl, p-tolyl, p-chlorophenyl, p-fluorophenyl, 2,4-dichlorophenyl, or 2,5-dichlorophenyl and m is defined as above; and the wavy line (ξ) represents the α or β configuration or mixtures thereof, which comprises:

a. treating the (dl) compounds of the formulas

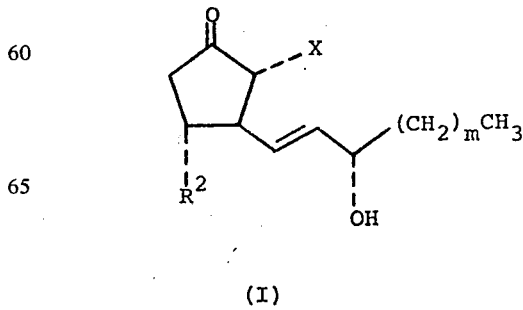

(I)

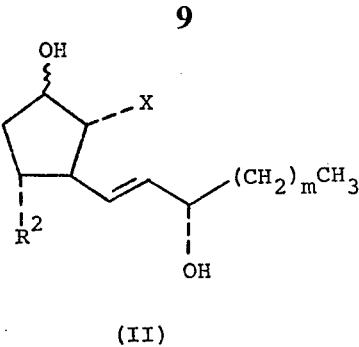

(II)

wherein X (including $R^1$ and m contained therein), $R^2$ and m are defined as above; with a substituted sulfenyl chloride compound of the formula $ClSR^3$, wherein $R^3$ is defined as above, in the presence of an amine base selected from the group consisting of triethylamine, N-methylpyrrolidine or pyridine, and an organic solvent to obtain the (dl) compounds of Formulas (A) and (B), respectively.

2. The process of claim 1 in which the amine base is triethylamine and the substituted sulfenyl compound is p-toluenesulfenyl chloride.

3. The process of claim 2 in which the starting material is a compound of Formula (I) and the product obtained is a compound of Formula (A).

4. The process of claim 3 in which the starting material is (dl)-2α-(6-carbomethoxyhexyl)-3β-(3α-hydroxy-trans-1-octenyl)-1-oxocyclopentane and the product obtained is (dl)-2α-(6-carbomethoxyhexyl)-3β-(1α-p-tolylsulfinyl-trans-2-octenyl)-1-oxycyclopentane.

5. The process of claim 3 in which the starting material is (dl)-2α-(6-carbomethoxy-cis-2-hexenyl)-3β-(3α-hydroxy-trans-1-octenyl)-1-oxocyclopentane and the product obtained is (dl)-2α-(6-carbomethoxy-cis-2-hexenyl)-3β-(1β-p-tolylsulfinyl-trans-2-octenyl)-1-oxocyclopentane.

6. The process of claim 3 in which the starting material is (dl)-2α-(6-carbomethoxyhexyl)-3β-(3α-hydroxy-trans-1-octenyl)-4α-hydroxy-1-oxocyclopentane and the product obtained is (dl)-2α-(6-carbomethoxyhexyl)-3β-(1α-p-tolylsulfinyl-trans-2-octenyl)-4α-hydroxy-1-oxocyclopentane.

7. The process of claim 3 in which the starting material is (dl)-2α-(6-carbomethoxy-cis-2-hexenyl)-3β-(3α-hydroxy-trans-1-octenyl)-4α-hydroxy-1-oxocyclopentane and the product obtained is (dl)-2α-(6-carbomethoxy-cis-2-hexenyl)-3β-(1α-p-tolylsulfinyl-trans-2-octenyl)-4α-hydroxy-1-oxocyclopentane.

8. The process of claim 2 in which the starting material is a compound of Formula (II) and the product obtained is a compound of Formula (B).

9. The process of claim 8 in which the starting material is (dl)-2α-(6-carbomethoxyhexyl)-3β-(3α-hydroxy-trans-1-octenyl)-1α-hydroxycyclopentane and the product obtained is (dl)-2α-(6-carbomethoxyhexyl)-3β-(1α-p-tolylsulfinyl-trans-2-octenyl)-1α-hydroxycyclopentane.

10. The process of claim 8 in which the starting material is (dl)-2α-(6-carbomethoxy-cis-2-hexenyl)-3β-(3α-hydroxy-trans-1-octenyl)-1α-hydroxycyclopentane and the product obtained is (dl)-2α-(6-carbomethoxy-cis-2-hexenyl)-3β-(1α-p-tolylsulfinyl-trans-2-octenyl)-1α-hydroxycyclopentane.

11. The process of claim 8 in which the starting material is (dl)-2α-(6-carbomethoxyhexyl)-3β-(3α-hydroxy-trans-1-octenyl)-4α-hydroxy-1α-hydroxycyclopentane and the product obtained is (dl)-2α-(6-carbomethoxyhexyl)-3β-(1α-p-tolylsulfinyl-trans-2-octenyl)-4α-hydroxy-1α-hydroxy-cyclopentane.

12. The process of claim 8 in which the starting material is (dl)-2α-(6-carbomethoxy-cis-2-hexenyl)-3β-(3α-hydroxy-trans-1-octenyl)-4α-hydroxy-1α-hydroxycyclopentane and the product obtained is (dl)-2α-(6-carbomethoxy-cis-2-hexenyl)-3β-(1α-p-tolylsulfinyl-trans-2-octenyl)-4α-hydroxy-1α-hydroxycyclopentane.

13. The process of claim 8 in which the starting material is (dl)-2α-(6-carbomethoxyhexyl)-3β-(3α-hydroxy-trans-1-octenyl)-1β-hydroxycyclopentane and the product obtained is (dl)-2α-(6-carbomethoxyhexyl)-3β-(1α-p-tolylsulfinyl-trans-2-octenyl)-1β-hydroxycyclopentane.

14. The process of claim 8 in which the starting material is (dl)-2α-(6-carbomethoxy-cis-2-hexenyl)-3β-(3α-hydroxy-trans-1-octenyl)-1β-hydroxycyclopentane and the product obtained is (dl)-2α-(6-carbomethoxy-cis-2-hexenyl)-3β-(1β-p-tolylsulfinyl-trans-2-octenyl)-1β-hydroxycyclopentane.

15. The process of claim 8 in which the starting material is (dl)-2α-(6-carbomethoxyhexyl)-3β-(3α-hydroxy-trans-1-octenyl)-4α-hydroxy-1β-hydroxycyclopentane and the product obtained is (dl)-2α-(6-carbomethoxyhexyl)-3β-(1α-p-tolylsulfinyl-trans-2-octenyl)-4α-hydroxy-1β-hydroxycyclopentane.

16. The process of claim 8 in which the starting material is (dl)-2α-(6-carbomethoxy-cis-2-hexenyl)-3β-(3α-hydroxy-trans-1-octenyl)-4α-hydroxy-1β-hydroxycyclopentane and the product obtained is (dl)-2α-(6-carbomethoxy-cis-2-hexenyl-3β-(1α-p-tolylsulfinyl-trans-2-octenyl)-4α-hydroxy-1β-hydroxycyclopentane.

* * * * *

UNITED STATES PATENT AND TRADEMARK OFFICE
CERTIFICATE OF CORRECTION

PATENT NO. : 3,975,427
DATED : August 17, 1976
INVENTOR(S) : KARL G. UNTCH

It is certified that error appears in the above—identified patent and that said Letters Patent are hereby corrected as shown below:

Column 9, Claim 5, line 38, "(1β-p-tolysulfinyl" should read --- (1α-p-tolylsulfinyl ---. Column 10, Claim 14, line 38, "(1β-p-" should read --- (1α-p- ---.

Signed and Sealed this

Ninth Day of November 1976

[SEAL]

Attest:

RUTH C. MASON
*Attesting Officer*

C. MARSHALL DANN
*Commissioner of Patents and Trademarks*